US008447010B2

(12) United States Patent
Reichel

(10) Patent No.: US 8,447,010 B2
(45) Date of Patent: May 21, 2013

(54) DEVICE FOR DATA TRANSFER, COMPUTED TOMOGRAPHY APPARATUS AND METHOD FOR DATA TRANSFER

(75) Inventor: Werner Reichel, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 335 days.

(21) Appl. No.: 12/977,125

(22) Filed: Dec. 23, 2010

(65) Prior Publication Data

US 2011/0150039 A1    Jun. 23, 2011

(30) Foreign Application Priority Data

Dec. 23, 2009   (DE) .......................... 10 2009 060 316

(51) Int. Cl.
*H04B 1/00*    (2006.01)
(52) U.S. Cl.
USPC ............................................. 378/19; 378/15

(58) Field of Classification Search
USPC ......................................................... 378/4–20
See application file for complete search history.

(56) References Cited

U.S. PATENT DOCUMENTS

| 7,274,765 | B2 * | 9/2007 | Krumme et al. | ................. 378/15 |
| 2004/0062344 | A1 * | 4/2004 | Popescu et al. | ................. 378/15 |
| 2007/0040635 | A1 * | 2/2007 | Popescu et al. | ................. 333/261 |

* cited by examiner

*Primary Examiner* — Hoon Song
(74) *Attorney, Agent, or Firm* — Schiff Hardin LLP

(57) ABSTRACT

In a device and a method for data transfer between a rotatable part and stationary part of a gantry of a computed tomography apparatus a broadband transmission link is used for data between the rotatable part and the stationary part of the gantry, via which both measurement data and operating data of the computed tomography apparatus are transferred. An arrangement also is provided for narrowband transmission of data of the computed tomography apparatus via the broadband transmission link. The data of the computed tomography apparatus are transmitted using a frequency spread method via the broadband transmission link.

16 Claims, 2 Drawing Sheets

DEVICE FOR DATA TRANSFER, COMPUTED TOMOGRAPHY APPARATUS AND METHOD FOR DATA TRANSFER

BACKGROUND OF THE INVENTION

1. Field of the Invention

The invention concerns a device and a method for data transfer between a rotatable part and a stationary part of a gantry of a computed tomography apparatus. The invention moreover concerns a computed tomography apparatus that embodies such a device for data transfer.

2. Description of the Prior Art

A computed tomography apparatus, in particular an x-ray computed tomography apparatus, has a gantry with a part that can rotate relative to a stationary part, on which rotatable part are arranged (among other things) an x-ray source and an x-ray detector opposite one another. In operation of the x-ray computed tomography apparatus, large quantities of measurement data accumulate due to the acquisition of numerous x-ray projections. This measurement data must be transferred from the rotating part of the gantry to the stationary part, since the processing of the measurement data (in particular the reconstruction of slice images and 3D images based on the measurement data) ensues with an image computer located at the stationary side.

Furthermore, in operation of the x-ray computed tomography apparatus, bidirectional operating data of the x-ray computed tomography apparatus (such as control data, status data etc.) must be transferred from the stationary part to the rotatable part of the gantry and from the rotatable part to the stationary part.

The data transfer between the stationary part of the gantry and the rotatable portion of the gantry can occur by mechanical contact by means of slip rings or without contact, for example by means of capacitive coupling. For example, in DE 10 2005 056 049 A1 a contactless data transfer by means of capacitive coupling in a computed tomography apparatus is described. At least one strip conductor (stripline) pair for symmetrical data transfer is mounted on the rotatable part of the gantry, into which conductor pair the data to be transferred, or electrical signals carrying the information, are fed by a transmission module. At least one receiver element is mounted on the stationary part. This receiver element is located along at least one segment of the strip conductor pair during the relative movement of the two parts with slight separation and is connected with a receiver module.

A computed tomography apparatus normally has multiple such data transfer (transmission) links, each having a strip conductor pair. A first data transmission link is present for the transfer of the measurement data acquired with the x-ray detector from the rotatable part to the stationary part of the gantry. A second data transmission link is provided for the transfer of operating data of the computed tomography apparatus from the stationary part to the rotatable part of the gantry, and a third data transmission link is provided for the transfer of operating data of the computed tomography apparatus from the rotatable part of the gantry to the stationary part. The second and third data transmission links serve for the generation of the redundancy necessary for the transfer of operating data in order to achieve a certain data transfer rate between the rotatable part of the gantry and the stationary part.

The provision and the parallel operation of the three transmission links for data represent a not inconsiderable technical and financial cost.

SUMMARY OF THE INVENTION

An object of the invention is to provide a device, a computed tomography apparatus and a method of the aforementioned type wherein the cost for the data transfer between the stationary part and rotatable part of the gantry of a computed tomography apparatus is reduced.

According to the invention, this object is achieved by a device for data transfer between a rotatable part and stationary part of a gantry of a computed tomography apparatus having a broadband transmission link for data between the rotatable part and the stationary part of the gantry, via which both measurement data and operating data of the computed tomography apparatus are transferred. The device also includes circuitry for narrowband transfer of data of the computed tomography apparatus via the broadband transmission link for data, and circuitry for broadband transfer of data of the computed tomography apparatus using a frequency spread method via the broadband transmission link for data.

The invention is based on the insight that the frequency bandwidth of the data transmission link to transfer the measurement data generated during the operation of a computed tomography apparatus with the x-ray detector is not utilized by the narrowband transfer of the measurement data, and thus existing transfer capacity of the data transmission link remains unutilized. This also applies for the two data transmission links for transfer of operating data of the computed tomography apparatus. Thus in accordance with the invention, a transfer (advantageously bidirectionally) of not only measurement data but also operating data of the computed tomography take place at the same time via only one broadband transmission link for data between the rotatable part and stationary part of the gantry.

Signals of a narrowband system and signals of a system that transfers data by means of frequency spreading thus coexist on only one physical, broadband transmission link for data without requiring a spectral separation of the signals of the two systems. A spread signal is distributed optimally broadly in the frequency band of the transmission link with a very low transmission power. For a receiver of the narrowband system the spread signal degrades into noise. The narrowband receiver receives only in a narrow frequency range of the frequency band of the transmission link. In contrast to this, a receiver of the broadband system can detect the spread signal. The spread signals normally do not interfere with the narrowband system since—as noted—they fall below the noise. A system which transfers data by means of frequency spreading thereby efficiently utilizes the bandwidth of the frequency band of the physical transmission link. A spread signal can itself be considered as an extended signal that cannot be affected by narrowband signals or interferences because they act only on a small portion of the broadly distributed spread signal. The receiver for the spread signal does not filter the incoming signal according to frequency but rather according to pulse shape. In order to avoid interference due to multiple path propagation, the signals are advantageously synchronized.

Two physical transmission links for data can be spared via this solution, which reduces not only the technical cost but also the financial cost for the data transfer between a rotating part and stationary part of a gantry of a computed tomography apparatus.

According to an embodiment of the invention, the broadband transfer of data of the computed tomography apparatus ensues in an ultra-wideband (UWB) technique that dictates the frequency spreading.

In another embodiment of the invention the broadband transmission link for data has a frequency bandwidth of 10 MHz to 20 GHz.

According to a further embodiment of the invention, the width of the frequency band for the narrowband transmission of data (which can be a baseband transmission) is between 10 MHz and 4.5 GHz.

In contrast to this, according to one variant of the invention the width of the frequency band for the broadband transmission of data by means of frequency spreading is between 5 GHz and 9 GHz.

Due to the frequency bandwidth of the broadband transmission link, the frequency bands for the narrowband transmission of data and the broadband transmission of data by means of frequency spreading can be completely separate from one another. However, the frequency bands for the narrowband transmission of data and the broadband transmission of data by means of frequency spreading can also intersect since, as mentioned, narrowband signals and spread signals do not interfere. The spread signals are additionally encoded with a spread code.

The data transmission via the broadband transmission link preferably takes place without contact, for example capacitively (as mentioned above).

According to one embodiment of the invention, the broadband transmission link possesses at least one annular transmission element into which the signals of the narrowband system and the spread signals are fed. The annular transmission element is a waveguide. In a capacitive transmission, the annular transmission element can be executed as a microstrip conductor or as a microstrip conductor pair for a differential transfer which is arranged on the rotatable part of the gantry, for example.

According to another variant of the invention, the narrowband data transmission means transfer the measurement data of the computed tomography apparatus via the broadband transmission link for data and possess at least one transmission device for narrowband transmission of measurement data that is arranged at the rotatable part of the gantry and at least one reception device arranged at the stationary part for a narrowband reception of measurement data. In principle, this variant of the invention does not change the manner of the transfer of the measurement data from the rotatable part to the stationary part of the gantry.

However, the behavior is different with the transmission of the operating data. According to a further variant of the invention the means to transmit data by means of frequency spreading likewise transmit via the broadband transmission link for data and for this possess at least one transmission device and at least one reception device at the rotatable part and stationary part of the gantry respectively for the broadband transmission of operating data by means of frequency spreading. The operating data are accordingly transmitted bidirectionally between rotatable part and stationary part of the gantry by means of frequency spreading. The data transfer preferably takes place in an ultra-wideband technique.

One embodiment of the invention provides that the means to transfer data of the computer tomography by means of frequency spreading or in an ultra-wideband technique are connected with a network, meaning that a network or a part of a network is present on the rotatable part and stationary part of the gantry. Among other things, controllers or control units on both the stationary part and the rotatable part of the gantry are connected to the network, which controllers or control units exchange data (in particular operating data) with one another via the network and the UWB system.

A further embodiment of the invention provides that the network is an Ethernet network. An Ethernet network has the advantage that a certain data transfer of the operating data can be realized since a necessary redundancy can be implemented at higher levels of the protocol stack. The redundancy provided by the two separate transmission links for operating data in the prior art can thus also be provided with only one physical transmission link.

The object of the invention is moreover achieved by a computed tomography apparatus that has a device as previously described for the data transmission between a rotatable part and a stationary part of a gantry.

The object of the invention also is achieved by a method for data transmission between a rotatable part and stationary part of a gantry of a computed tomography apparatus in which measurement data and operating data of the computed tomography apparatus are transferred via a broadband transmission link for data between the rotatable part and stationary part of the gantry, wherein the transmission of the data occurs via narrowband and using a frequency spreading method, in particular in an ultra-wideband technique. A simultaneous transmission of different data normally ensues via the transmission link, wherein measurement data of the computed tomography apparatus are preferably transmitted via narrowband and operating data of the computed tomography apparatus are preferably transferred using the frequency spread method.

DESCRIPTION OF THE PREFERRED EMBODIMENTS

Figure 1:
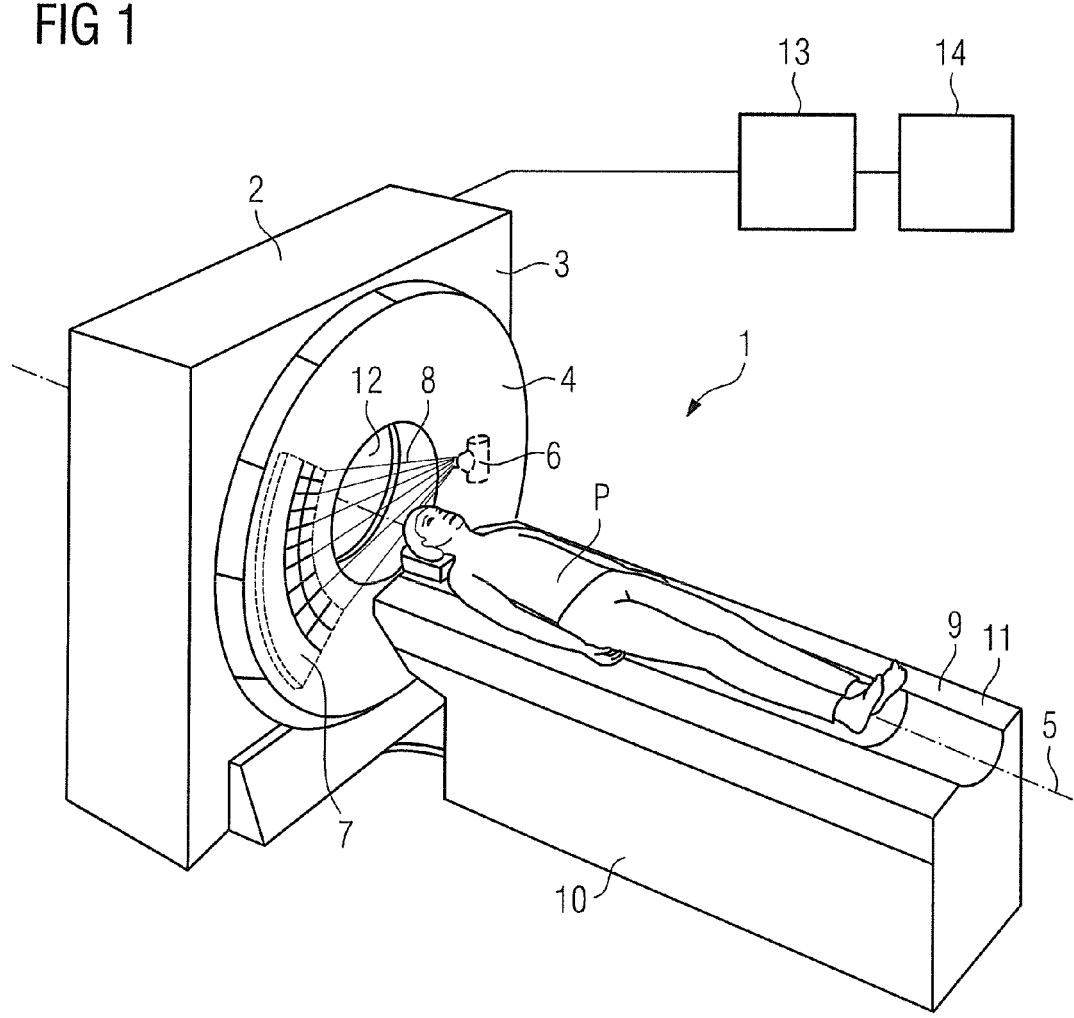
FIG. 1 illustrates an x-ray computed tomography apparatus.

Identical or functionally identical elements in figures are provided throughout with the same reference characters. The representations in figures are schematic and not necessarily true to scale. In the following the x-ray computed tomography apparatus 1 shown in FIG. 1 and FIG. 2 is discussed without limitation of the generality and only insofar as it is deemed necessary to understand the invention.

Figure 2:
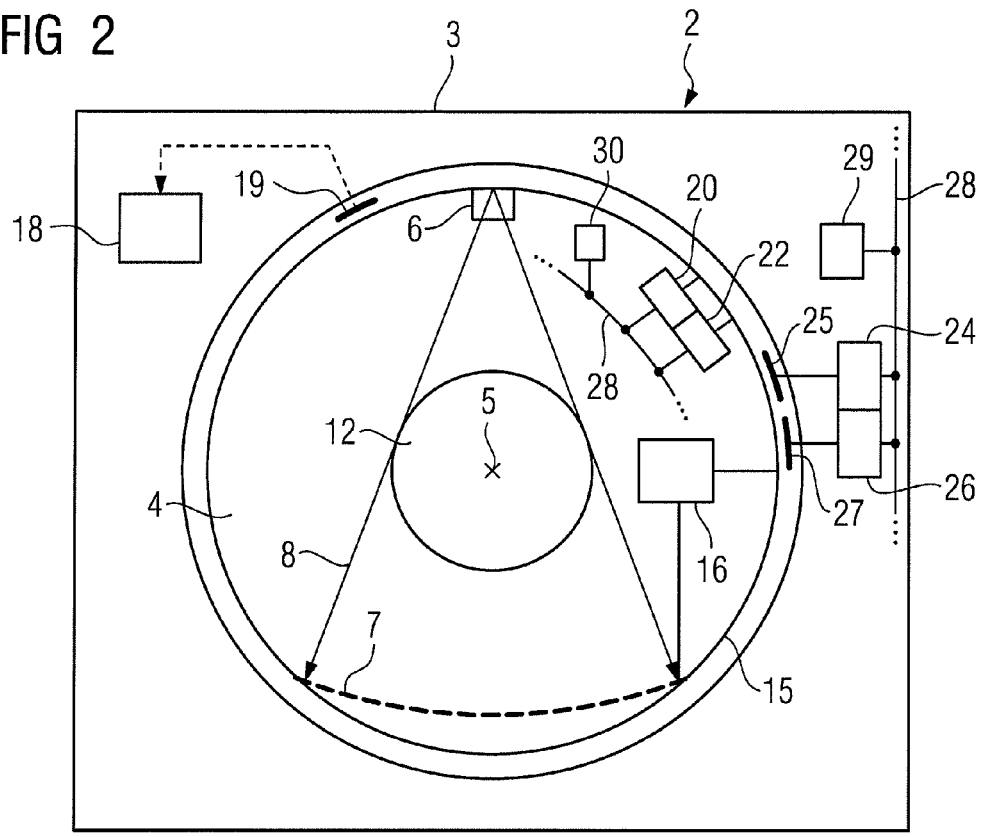
FIG. 2 is a cross section view of the gantry of the x-ray computed tomography apparatus from FIG. 1.

The x-ray computed tomography apparatus 1 shown in FIG. 1 has a gantry 2 with a stationary part 3 and with a part 4 that can rotate around a system axis 5. In the case of the present exemplary embodiment of the invention the rotatable part 4 possesses an x-ray system which comprises an x-ray source 6 and an x-ray detector 7 that are arranged opposite one another on the rotatable part 4. In the operation of the x-ray computed tomography apparatus 1 x-ray radiation 8 emanates from the x-ray source 6 in the direction of the x-ray detector 7, penetrates a measurement subject and is detected by the x-ray detector 7 in the form of measurement data or, respectively, measurement signals.

The x-ray computed tomography apparatus 1 furthermore has a patient bed 9 to bear a patient P to be examined. The patient bed 9 has a bed base 10 on which is arranged a patient bearing plate 11 provided to actually bear the patient P. The patient bearing plate 11 is adjustable relative to the bed base 10 in the direction of the system axis 5 such that it—together with the patient P—can be inserted into the opening 12 of the gantry 2 (which presently defines a cylindrical measurement field) to acquire 2D x-ray projections of the patient P, for example in a spiral scan. The computational processing of the 2D x-ray projections acquired with the x-ray system and the reconstruction of slice images, 3D images or a 3D data set based on the measurement data or measurement signals of the 2D x-ray projections ensues with an image computer 13 of the x-ray computed tomography apparatus 1, which slice images or 3D images can be presented on a display device 14.

In the operation of the x-ray computed tomography apparatus 1, operating data about operating states of components, control data and regulation data are to be transferred both from the stationary part 3 of the gantry to the rotatable part 4 and from the rotatable part 4 of the gantry to the stationary part 3. Furthermore, large quantities of measurement data acquired with the x-ray detector 7 are to be transferred from the rotatable part 4 to the stationary part 3. According to the invention, this takes place over only one physical, broadband transmission link for data.

In the exemplary embodiment of the invention, the data transmission ensues without contact (and in fact capacitively) via the interface between the stationary part 3 and the rotatable part 4. For this purpose, in the exemplary embodiment of the invention the rotatable part 4 of the gantry 2 has an annular microstrip conductor pair 15 with closed microstrip conductors along its periphery. The microstrip conductor pair 15 or waveguide pair 15 represents the broadband transmission link for data that has a frequency bandwidth of 10 MHz to 20 GHz.

The arrangement of the microstrip conductor pair 15 on the rotatable part 4 is illustrated perpendicular to the system axis 5 of the gantry 2 of the x-ray computed tomography 1 in the schematic cross section view.

In the exemplary embodiment of the invention, a transmission device or transmitter 16 for a narrowband transmission of the measurement data of the x-ray detector 7 that are acquired in the operation of the x-ray computed tomography apparatus 1 is connected with the x-ray detector 7. The transmitter 16 feeds signals carrying measurement information into the microstrip conductor pair 15. A receiver device or a receiver 18 and a receiver antenna 19 for narrowband reception of signals carrying the measurement information are present at the stationary part 3. The signals carrying measurement information that are received with the receiver antenna 19 and the receiver 18 are evaluated by the receiver 18 to recover the measurement data, which measurement data are relayed to the image computer 13. In the present exemplary embodiment of the invention, the narrowband transmission of the measurement data is a baseband transmission. The width of the frequency band is presently approximately 4 GHz.

In the exemplary embodiment of the invention, operating data of the x-ray computed tomography apparatus 1 are simultaneously transmitted in parallel, or dependent on incoming data, via the microstrip conductor pair 15 with an ultra-wideband technique in which a frequency spreading of the signals to be transferred is conducted. For this purpose, at least one UWB transmission device or an UWB transmitter 20 and an UWB reception device or UWB receiver 22 are connected with the microstrip conductor pair 15 at the rotatable part 4. Furthermore, at least one UWB transmission device or UWB transmitter 24 and an UWB transmitter antenna 25 and an UWB reception device or UWB receiver 26 and an UWB receiver antenna 27 are arranged at the stationary part 3. UWB signals fed into the microstrip conductor pair 15 from the UWB transmitter 20 or from the UWB transmitter 24 via the UWB antenna 25 can be correspondingly received with the UWB receiver 26 via the UWB antenna 27 or with the UWB receiver 22.

In the exemplary embodiment of the invention, the UWB transmitters 20 and 24 and the UWB receivers 22 and 26 are connected to an Ethernet network. Additional components of the x-ray computed tomography apparatus 1 for data exchange among one another on the Ethernet network are connected via transceivers (not shown) at both the stationary part 3 and the rotatable part 4. It is shown by way of example in FIG. 2 that a controller 19 at the stationary part 3 is connected to the Ethernet network 28 and a controller 30 at the rotatable part 4 is connected to the Ethernet network 28 in order to be able to exchange operating data with one another. As a network, Ethernet 28 has the advantage that the redundancy necessary for the transmission of operating data can be provided in a higher protocol stack. The width of the frequency band for the transmission of operating data with an ultra-wideband technique is presently between 5 GHz and 9 GHz.

Figure 3:
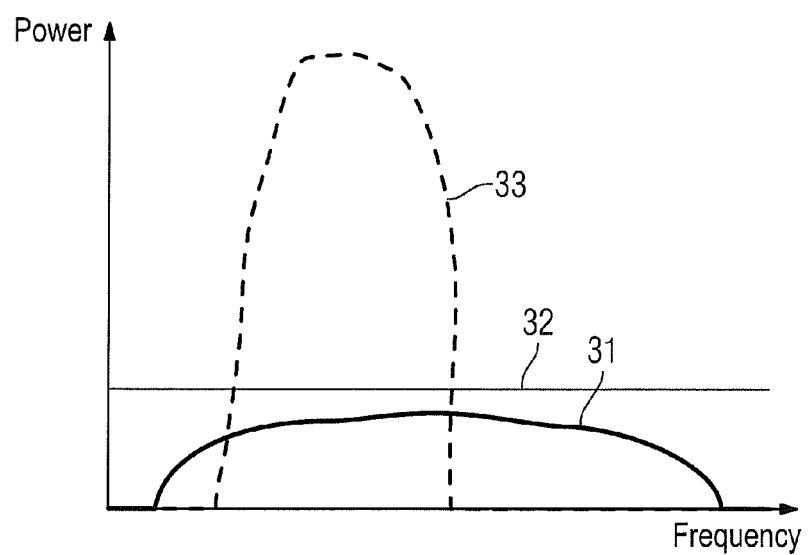
FIG. 3 is an illustration of the narrowband transmission of measurement data and the transmission of operating data in an UWB technique.

In the data transmission via the microstrip conductor pair 15, signals 33 carrying measurement information with relatively high power and transmitted in a narrow frequency band and UWB signals 31 carrying operating information with a very low transmission power and distributed or spread widely in the frequency band of the transmission link thus coexist. As is illustrated in FIG. 3, the UWB signals of the UWB system descend into thermal noise 32 for the receiver 18 of the narrowband system. The receiver 18 receives only in a narrow frequency range of the frequency band of the transmission link.

In contrast to this, the UWB receivers 22 and 26 of the UWB system can detect and receive the UWB signals fed into the microstrip conductor pair 15. The UWB signals do not interfere with the narrowband system since, as already mentioned, they fall below the noise 32. The UWB system efficiently utilizes the frequency band of the transmission link. The UWB signals themselves can be considered as stretched signals which are not affected by the signals of the narrowband system because they act on only a small portion of the broadly distributed UWB signals. The UWB receivers 22 and 26 thereby do not filter the incoming signals according to frequency but rather according to pulse shape. The UWB signals are additionally encoded.

Moreover, the frequency spectra of the narrowband system and of the UWB system do not need to intersect but rather can be separate from one another.

In contrast to the described exemplary embodiment of the invention, multiple UWB transmission devices and UWB reception devices can be present both on the rotatable part 4 and on the stationary part 3.

Another technique for data transfer in which a frequency spreading of the signals to be transmitted is conducted can also be used instead of the UWB technique.

Instead of Ethernet, a different network can also be provided as a communication network for the x-ray computed tomography apparatus.

The specifications regarding the frequency bandwidth of the transmission channel, the width of the frequency band for the narrowband transmission of data and the width of the frequency band for the broadband transmission of data by means of frequency spreading are to be understood merely as examples and can also deviate from these examples.

The annular transmission element also does not necessarily have to be a microstrip conductor. Rather, the annular transmission element can also be a different waveguide, for example a hollow conductor.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device for transferring data in a computed tomography apparatus, comprising:
   a broadband transmission link configured for broadband transmission of apparatus data, selected from the group consisting of first data and second data different from said first data, between a stationary part of a gantry of the computed tomography apparatus and a rotatable part of the gantry;
   a narrowband transmission arrangement in communication with said broadband transmission link, said narrow band transmission arrangement being configured for narrowband transmission of said first data via the broadband transmission link between said stationary part and said rotatable part; and
   a broadband transmission arrangement in communication with said broadband transmission link, said broadband transmission arrangement being configured for broadband transfer of said second data using a frequency spread method via the broadband transmission link between said stationary part and said rotatable part.

2. A device as claimed in claim 1 wherein said broadband transmission arrangement is configured for broadband transmission of said second data by frequency spreading in an ultra-wide band technique.

3. A device as claimed in claim 1 wherein said broadband transmission link has a frequency bandwidth in a range between 10 MHz and 20 GHz.

4. A device as claimed in claim 3 wherein said narrowband transmission arrangement is configured to transmit said first data in a frequency band having a width in a range between 10 MHz and 4.5 GHz.

5. A device as claimed in claim 4 wherein said broadband transmission arrangement is configured for broadband transmission of said second data by frequency spreading in a frequency band having a range between 5 GHz and 9 GHz.

6. A device as claimed in claim 1 wherein said broadband transmission link is configured to transmit said apparatus data without electrical galvanic contacts.

7. A device as claimed in claim 1 wherein said broadband transmission link comprises at least one annular transmission element.

8. A device as claimed in claim 1 wherein said narrowband transmission arrangement comprises at least one transmission device for narrowband transmission of said first data located at said rotatable part, and at least one reception device for narrowband reception of said first data at said stationary part.

9. A device as claimed in claim 1 wherein said broadband transmission arrangement comprises at least one transmission device located at said rotatable part and at least one reception device located at said stationary part.

10. A device as claimed in claim 1 wherein said broadband transmission arrangement comprises a connection configured for placing said broadband transmission arrangement in communication with a network.

11. A device as claimed in claim 10 wherein said connection is configured for connection to an Ethernet network.

12. A device as claimed in claim 1 wherein said first data are measurement data of said computed tomography apparatus and said second data are operating data of said computed tomography apparatus.

13. A computed tomography apparatus comprising:
    a gantry comprising a stationary part and a rotatable part that rotates relative to said stationary part;
    a broadband transmission link configured to transmit apparatus data, selected from the group consisting of first data and second data that are different from said first data, between said stationary part and said rotatable part;
    a narrowband transmission arrangement in communication with said broadband transmission link, said narrow band transmission arrangement being configured for narrowband transmission of said first data via the broadband transmission link between said stationary part and said rotatable part; and
    a broadband transmission arrangement in communication with said broadband transmission link, said broadband transmission arrangement being configured for broadband transfer of said second data using a frequency spread method via the broadband transmission link between said stationary part and said rotatable part.

14. A computed tomography apparatus as claimed in claim 13 wherein said first data are measurement data of said computed tomography apparatus and said second data are operating data of said computed tomography apparatus.

15. A method for transmitting data between a rotatable part and a stationary part of a gantry of a computed tomography apparatus, comprising the steps of:
    providing a broadband transmission link configured for broadband transmission of apparatus data, selected from the group consisting of first data and second data that are different from said first data, between a stationary part of a gantry of the computed tomography apparatus and a rotatable part of the gantry;
    placing a narrowband transmission arrangement in communication with said broadband transmission link and, via said narrow band transmission arrangement, conducting narrowband transmission of said first data via the broadband transmission link between said stationary part and said rotatable part; and
    from a broadband transmission arrangement in communication with said broadband transmission link, implementing broadband transfer of said first data using a frequency spread method via the broadband transmission link between said stationary part and said rotatable part.

16. A method as claimed in claim 14 wherein said first data are measurement data of said computed tomography apparatus and said second data are operating data of said computed tomography apparatus.

* * * * *